US00PP37312P2

(12) United States Plant Patent
Vitten et al.

(10) Patent No.: US PP37,312 P2
(45) Date of Patent: Mar. 10, 2026

(54) RASPBERRY PLANT NAMED 'DrisRaspTwentyFive'

(50) Latin Name: ***Rubus idaeus* L**
Varietal Denomination: DrisRaspTwentyFive

(71) Applicant: Driscoll's, Inc., Watsonville, CA (US)

(72) Inventors: Matthias D. Vitten, Aptos, CA (US); Kyle Rak, Salinas, CA (US); Luis Miguel Rodriguez, Ciudad Guzman (MX); Stephanie Castro, Ventura, CA (US); Lluvia V. Gutierrez, Salinas, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 19/278,561

(22) Filed: Jul. 23, 2025

(51) Int. Cl.
*A01H 5/08* (2018.01)
*A01H 6/74* (2018.01)

(52) U.S. Cl.
USPC ..... Plt./204
CPC ..... *A01H 6/7499* (2018.05); *A01H 5/08* (2013.01)

(58) Field of Classification Search
USPC ..... Plt./156, 203, 204
See application file for complete search history.

(56) References Cited

U.S. PATENT DOCUMENTS

PP8,022 P 11/1992 Wilhelm
PP8,027 P 11/1992 Wilhelm
PP9,340 P 10/1995 Wilhelm et al.
PP9,653 P 10/1996 Wilhelm et al.
PP9,696 P 11/1996 Fear
PP11,067 P 9/1999 Fear et al.
PP11,087 P 10/1999 Fear et al.
PP11,094 P 10/1999 Fear et al.
PP11,102 P 10/1999 Fear et al.
PP14,761 P2 5/2004 Fear et al.
PP14,781 P2 5/2004 Fear et al.
PP14,804 P2 5/2004 Fear et al.
PP14,860 P2 6/2004 Fear et al.
PP14,903 P2 6/2004 Fear et al.
PP14,904 P2 6/2004 Fear et al.
PP18,658 P3 3/2008 Fear et al.
PP18,659 P3 3/2008 Fear et al.
PP19,137 P3 8/2008 Harrison et al.
PP19,656 P2 1/2009 Hamilton et al.
PP22,246 P3 11/2011 Hamilton et al.
PP22,731 P2 5/2012 Fear et al.
PP23,477 P3 3/2013 Hamilton et al.
PP24,610 P3 7/2014 Hamilton et al.
PP25,044 P3 11/2014 Hamilton et al.
PP25,045 P3 11/2014 Hamilton et al.
PP27,644 P3 2/2017 Hamilton et al.
PP28,401 P3 * 9/2017 Swartz ..... Plt./204
PP28,775 P2 12/2017 Hamilton et al.
PP28,856 P3 1/2018 Hamilton et al.
PP29,402 P2 6/2018 Vitten et al.
PP30,577 P2 6/2019 Vitten et al.
PP30,733 P2 7/2019 Hamilton et al.
PP31,850 P2 6/2020 Hamilton et al.
PP32,496 P2 11/2020 Vitten et al.
PP32,722 P2 1/2021 Vitten et al.
PP33,723 P2 12/2021 Vitten et al.
PP33,736 P2 12/2021 Vitten et al.
PP33,758 P2 12/2021 Vitten et al.
PP34,070 P2 3/2022 Vitten et al.
PP35,578 P2 1/2024 Hamilton et al.
PP35,903 P2 7/2024 Vitten et al.

* cited by examiner

*Primary Examiner* — Karen M Redden
(74) *Attorney, Agent, or Firm* — Morrison & Foerster LLP

(57) ABSTRACT

A new and distinct variety of raspberry plant named 'DrisRaspTwentyFive', particularly selected for its early fruiting, consistent fruit size and shape, deep red color, and sweet flavor, is disclosed.

3 Drawing Sheets

Latin name: Botanical classification: *Rubus idaeus* L.

Varietal denomination: The varietal denomination of the claimed variety of raspberry plant is 'DrisRaspTwentyFive'.

BACKGROUND OF THE INVENTION

Raspberries are the edible fruit of a multitude of plant species in the genus *Rubus* of the rose family. Most raspberry species are in the subgenus Idaeobatus. Raspberry plants are perennial plants with woody stems. Many of the most important modern commercial red raspberry cultivars derive from hybrids between *R. idaeus* and *R. strigosus*. Recent breeding bas resulted in cultivars that are thornless and more strongly upright, not needing staking.

Both the red and the black raspberry species have albino-like pale-yellow natural or horticultural variants. Fruits from such plants are called golden raspberries or yellow raspberries. Most pale-fruited raspberries commercially sold in the eastern United States are derivatives of red raspberries. Yellow-fruited variants of the black raspberry are sometimes grown in home gardens. Despite their dissimilar appearance, golden raspberries retain the distinctive flavor of their respective red or black species.

An individual raspberry fruit is made up of around 100 drupelets, each of which contains a juicy pulp and a single central seed. A raspberry bush can yield several hundred berries a year. Unlike blackberries and dewberries, a raspberry has a hollow core once it is removed from the receptacle.

Raspberries are traditionally planted in the winter as dormant canes, but planting plugs produced by tissue culture is also common. Additionally, the long cane production method consists of growing canes for one year in cold climates where the bud break is early, and then transplanting the canes to warm climates where they quickly flower and can produce an early season crop. A very vigorous crop, raspberries spread well and can be considered invasive, using extended underground shoots (also known as suckers or basal shoots) that can develop roots and individual plants.

Raspberries are a popular fruit that are recognized for their antioxidants, high fiber, and as a good source of vitamin C. Raspberry fruit is typically consumed as fresh fruit, individually quick frozen (IQF) fruit, or in prepared foods, such as purées, juices, jellies, jams, grocery items, baked goods, and snack foods.

Raspberry is an important and valuable commercial fruit crop, widely grown in all temperate regions of the world. Accordingly, there is a need for new varieties of raspberry plant. In particular, there is a need for improved varieties of raspberry plant that are stable, high yielding, and agronomically sound.

SUMMARY OF THE INVENTION

In order to meet these needs, the present invention is directed to an improved variety of raspberry plant. In particular, the invention relates to a new and distinct variety of raspberry plant (*Rubus idaeus* L.), which has been denominated as 'DrisRaspTwentyFive'.

Raspberry plant variety 'DrisRaspTwentyFive' was selected in Santa Cruz County, California in September of 2018 and originated from a cross between the proprietary female parent 'RH780.1' (unpatented) and the male parent 'DrisRaspSeventeen' (U.S. Plant Pat. No. 32,722). The original seedling of the new variety was first asexually propagated in Santa Cruz County, California via root cuttings in November 2019.

'DrisRaspTwentyFive' was subsequently asexually propagated via root cuttings, and has undergone testing in Santa Cruz County, California for six years (2019 to 2025). The present variety has been found to be stable and reproduce true to type through successive asexual propagations via root cuttings and tissue culture.

'DrisRaspTwentyFive' was particularly selected for its early fruiting, consistent fruit size and shape, deep red color, and sweet flavor.

BRIEF DESCRIPTION OF THE DRAWINGS

This new raspberry plant is illustrated by the accompanying photographs. The colors shown are as true as can be reasonably obtained by conventional photographic procedures. The photographs are of plants that are two years old.

DETAILED BOTANICAL DESCRIPTION

Figure 1:
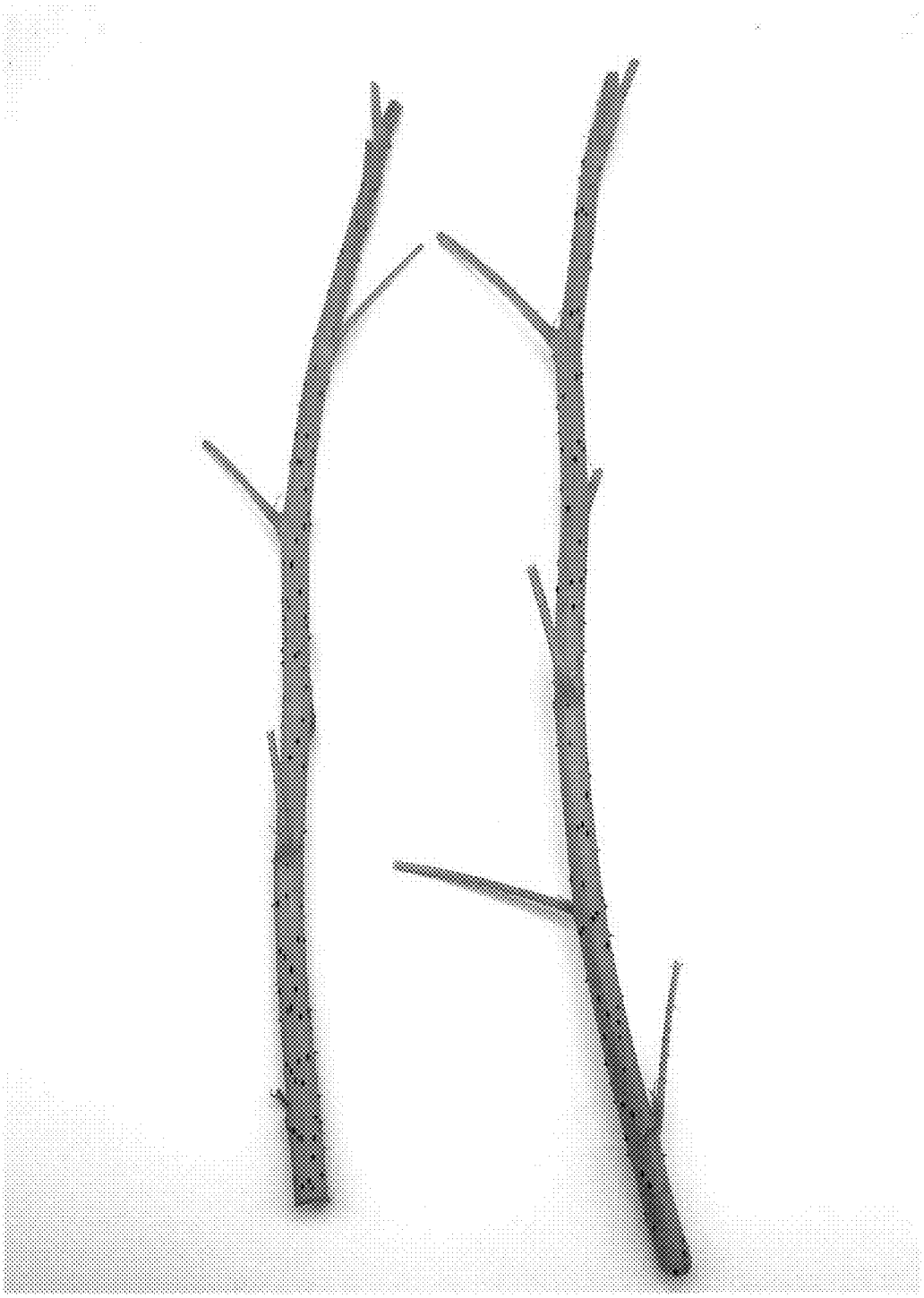
FIG. 1 illustrates sections of canes of raspberry variety 'DrisRaspTwentyFive'.
Figure 2:
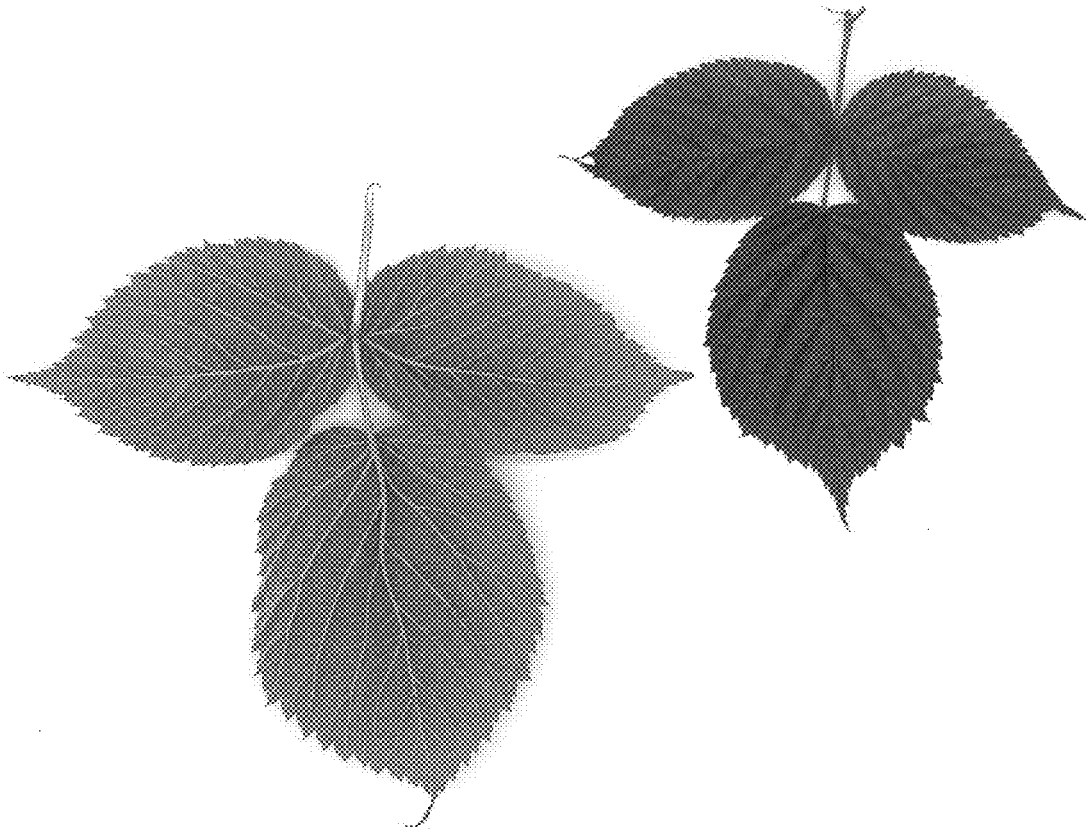
FIG. 2 illustrates the leaves of raspberry variety 'DrisRaspTwentyFive'.
Figure 3:
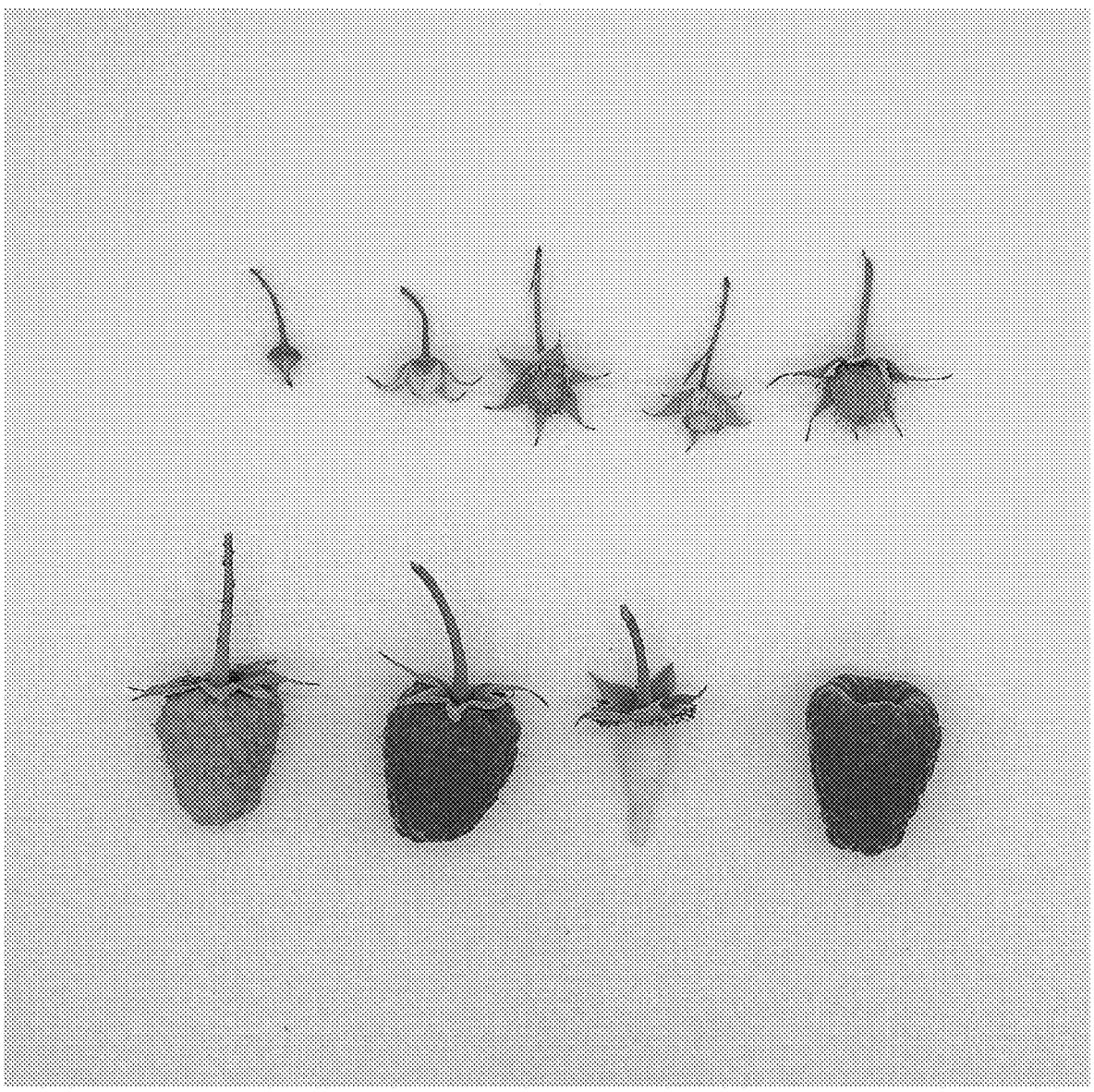
FIG. 3 illustrates flowers and fruit of raspberry variety 'DrisRaspTwentyFive' at various stages of development.

The following descriptions set forth the distinctive characteristics of 'DrisRaspTwentyFive'. Unless where otherwise noted, the data that define these characteristics are based on observations taken from 'DrisRaspTwentyFive' plants that were two years old, grown in Santa Cruz County, California from 2019 to 2025. These descriptions are in accordance with UPOV terminology. Color designations, color descriptions, and other phenotypical descriptions may deviate from the stated values and descriptions depending upon variation in environmental, seasonal, climatic and cultural conditions. 'DrisRaspTwentyFive' has not been observed under all possible environmental conditions. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G, Harris and Melinda Woolf Harris, unless where otherwise defined.

Classification:

*Family*.—Rosaceae.

*Botanical*.—*Rubus idaeus* L.

*Common name*.—Raspberry.

*Variety name*.—'DrisRaspTwentyFive'.

Parentage:

*Female parent*.—'RH780.1' (unpatented).

*Male parent*.—'DrisRaspSeventeen' (U.S. Plant Pat. No. 32,722).

Plant:

*Height*.—222 cm.

*Width*.—152 cm.

*Length/width ratio*.—1.46.

*Growth habit*.—Semi-upright.

*Self-fruitness*.—Self-fruitful.

*Time of vegetative bud burst*.—mid-April.

*Time of cane emergence*.—Late April to early May.

*Primocane* (*current year's cane*).—Cane length: 245 cm. Cane diameter: 0.93 cm. Internodal distance at central ⅓ of cane: 5.23 cm. Vegetative bud length at central ⅓ of cane: 4.94 mm. Anthocyanin coloration of cane: Absent. Cane color: RHS 144A (Strong yellow green). Cane bloom: Very weak. Shape of cane in cross-section: Rounded to angular. Pubescence: Absent.

*Very young shoot*.—Anthocyanin coloration of apex during rapid growth: Absent.

*Floricane* (*previous year's cane*).—Cane length: 145.1 cm. Cane diameter: 1.5 cm. Dormant cane color: RHS 200B (Greyish reddish brown). Fruiting lateral attitude: Semi-upright. Fruiting lateral length: 42.5 cm.

*Prickles* (*spines*).—Presence: Present. Density: Medium. Diameter (at base): 0.41 mm. Length (from base to tip): 1.67 mm. Color: RHS N186 (Dark greyish red). Attitude of tip: Horizontal. Presence and distribution on petioles: Present and regularly distributed.

Leaves:

*Predominant number of leaflets*.—Three.

*Color of upper side*.—RHS N138B (Moderate yellowish green).

*Color of lower side*.—RHS 138A (Moderate yellowish green).

*Glossiness*.—Medium.

*Arrangement of leaflets*.—Free.

*Arrangement*.—Opposite.

*Terminal leaflet*.—Length: 10 cm. Width: 7 cm. Length/width ratio: 1.43. Overall shape: Ovate. Shape of apex: Convex. Shape of base: Obtuse. Margin: Serrate. Profile in cross section: Concave. Undulation: Medium.

*Lateral leaflets*.—Length: 10.3 cm. Width: 7.1 cm. Length/width ratio: 1.46. Length to stalklet: 2.37 mm. Overall shape: Ovate. Shape of apex: Convex. Shape of base: Obtuse. Margin: Serrate.

*Rachis length between terminal leaflet and adjacent lateral leaflets*.—35.0 mm.

*Petiole*.—Length: 61.66 mm. Diameter: 3.22 mm. Color: RHS N138B (Moderate yellowish green).

*Stipule*.—Orientation: Erect.

Flowers:

*Percent of cane flowering on primocanes*.—60%.

*Diameter*.—13.93 mm.

*Petal*.—Length: 7.98 mm. Width: 3.87 mm. Length/width ratio: 2.06. Color: RHS NN155B (White).

*Pedicel*.—Length: 36.39 mm. Diameter: 1.20 mm. Number of spines on pedicel: 25. Color: RHS 143C (Strong yellow green). Anthocyanin coloration: Absent.

*Peduncle*.—Length: 31.87 mm. Diameter: 1.60 mm. Color: RHS 140A (Vivid yellow). Anthocyanin coloration: Absent.

Fruit:

*Length*.—29.52 mm.

*Diameter*.—25.26 mm.

*Length/width ratio*.—1.17.

*Weight* (*primocane*).—6.5 g/fruit.

*Weight* (*floricane*).—5.7 g/fruit.

*Sweetness/soluble solids* (° *Brix*).—10.2.

*Titratable acidity* (% *as citric acid*).—1.8%.

*Length of single drupe*.—6.29 mm.

*Diameter of single drupe*.—4.98 mm.

*Average number of drupes per fruit*.—130.

*Shape of fruit in lateral view*.—Conical.

*Color*.—RHS 46A (Strong red).

*Glossiness*.—Medium.

*Firmness*.—Medium.

*Color of torus at distal end*.—RHS 53D (Strong red).

*Adherence to torus*.—Medium.

*Seed*.—Weight: 0.0037 g/seed.

Production:

*Main bearing type*.—Both on previous year's cane in summer (floricane) and on current year's cane in autumn (primocane).

*Primocane* (*current year's cane*).—Time of beginning of flowering: Early June. Time of beginning of fruit ripening: Mid July. Percent of yield from primocane: 70% of total yield. Yield: 17,000 kg to 17,800 kg of marketable fruit per hectare per primocane crop when grown in Watsonville, California.

*Floricane* (*previous year's cane*).—Time of beginning of flowering: Late April. Time of beginning of fruit ripening: Mid May. Yield: 14,000 kg to 14,300 kg of marketable fruit per hectare per floricane crop from when grown in Watsonville, California.

COMPARISONS TO PARENTAL AND REFERENCE RASPBERRY VARIETIES

'DrisRaspTwentyFive' differs from the proprietary female parent 'RH780.1' (unpatented) in that 'DrisRaspTwentyFive' fruit has an improved flavor, larger size, and has improved shipping and storage quality as compared to 'RH780.1'.

'DrisRaspTwentyFive' differs from the male parent 'DrisRaspSeventeen' (U.S. Plant Pat. No. 32,722) in that 'DrisRaspTwentyFive' has medium prickle density on the central third of current season's canes, absent anthocyanin coloration on current season's cane, medium fruit firmness, and the fruit length is long, whereas 'DrisRaspSeventeen' has sparse prickle density on the central third of current season's canes, weak anthocyanin coloration on current season's cane, the fruit firmness is soft, and the fruit length is medium. Additionally, 'DrisRaspTwentyFive' has improved shipping and storage quality as compared to 'DrisRaspSeventeen'.

'DrisRaspTwentyFive' differs from reference raspberry variety 'Driscoll Maravilla' (U.S. Plant Pat. No. 14,804) in that for 'DrisRaspTwentyFive' the time of vegetative bud burst is early to medium, the predominant number of leaflets is three, the fruit firmness is medium, and the arrangement of leaflets is free, whereas for 'Driscoll Maravilla' the time of vegetative bud burst is late, the predominant number of leaflets is five, the fruit firmness is firm, and the arrangement of leaflets is overlapping.

'DrisRaspTwentyFive' differs from reference raspberry variety 'DrisRaspTwelve' (U.S. Plant Pat. No. 30,577) in that 'DrisRaspTwentyFive' has medium prickle density on the central third of current season's canes, medium green color of the upper leaf side, conical fruit shape in lateral view, and dark red fruit color, whereas 'DrisRaspTwelve' has sparse prickle density on the central third of current season's canes, dark green color of the upper leaf side, trapezoidal fruit shape in lateral view, and light orange fruit color.

What is claimed is:

1. A new and distinct variety of raspberry plant designated 'DrisRaspTwentyFive' as shown and described herein.

* * * * *